(12) United States Patent
Hilfinger et al.

(10) Patent No.: US 8,535,716 B2
(45) Date of Patent: Sep. 17, 2013

(54) METHODS AND COMPOSITION OF EXTENDED DELIVERY OF WATER INSOLUBLE DRUGS

(75) Inventors: John Hilfinger, Ann Arbor, MI (US); Jae Seung Kim, Ann Arbor, MI (US); Paul Kijek, Whitmore Lake, MI (US)

(73) Assignee: TSRL, Inc., Ann Arbor, MI (US)

( * ) Notice: Subject to any disclaimer, the term of this patent is extended or adjusted under 35 U.S.C. 154(b) by 2928 days.

(21) Appl. No.: 11/097,487

(22) Filed: Apr. 1, 2005

(65) Prior Publication Data

US 2005/0220876 A1 Oct. 6, 2005

Related U.S. Application Data

(60) Provisional application No. 60/558,712, filed on Apr. 1, 2004.

(51) Int. Cl.
*A61K 9/22* (2006.01)

(52) U.S. Cl.
USPC ........... 424/468; 424/464; 424/465; 424/469; 424/470

(58) Field of Classification Search
None
See application file for complete search history.

(56) References Cited

U.S. PATENT DOCUMENTS

| | | | |
|---|---|---|---|
| 4,895,726 A | 1/1990 | Curtet et al. | |
| 4,994,273 A * | 2/1991 | Zentner et al. | 424/422 |
| 5,686,133 A | 11/1997 | Amidon et al. | 427/2.22 |
| 5,834,022 A | 11/1998 | Amidon et al. | 424/492 |
| 5,851,275 A | 12/1998 | Amidon et al. | 106/148.1 |
| 5,871,776 A * | 2/1999 | Mehta | 424/462 |
| 6,235,311 B1 * | 5/2001 | Ullah et al. | 424/472 |
| 6,375,966 B1 | 4/2002 | Maleeny et al. | |
| 6,462,093 B1 | 10/2002 | Miyamoto et al. | |
| 6,576,264 B1 | 6/2003 | Henriksen et al. | |
| 6,635,396 B2 | 10/2003 | Honeycutt et al. | |
| 6,844,459 B2 | 1/2005 | Hauer et al. | |
| 2002/0165134 A1 | 11/2002 | Richter et al. | |
| 2006/0141028 A1 | 6/2006 | Flashner-Barak et al. | |
| 2008/0139392 A1 | 6/2008 | Acosta-Zara et al. | |

FOREIGN PATENT DOCUMENTS

| | | |
|---|---|---|
| GB | 2 380 673 | 4/2003 |
| WO | WO 2008/047201 | 4/2008 |

OTHER PUBLICATIONS

Explotab, JRS Pharma LP, Mar. 2003, TDS.QAO.10020.00000.3, pp. 1-4.

* cited by examiner

*Primary Examiner* — James Rogers
(74) *Attorney, Agent, or Firm* — Gifford, Krass, Sprinkle, Anderson & Citkowski, P.C.

(57) ABSTRACT

A pharmaceutical composition is provided that includes an active ingredient in the form of a powder or granule, a water soluble high molecular weight excipient and a water insoluble hydrophilic amphiphilic excipient. These ingredients are solution mixed and dried to form a modified pharmaceutical ingredient in simultaneous contact with both the water soluble high molecular weight excipient and the water insoluble hydrophilic amphiphilic excipient. Adjuvants are compacted about the modified pharmaceutical ingredient as well as a release control agent. The release control agent being present at levels from 1 to 40 total weight percent of the pharmaceutical composition.

27 Claims, 5 Drawing Sheets

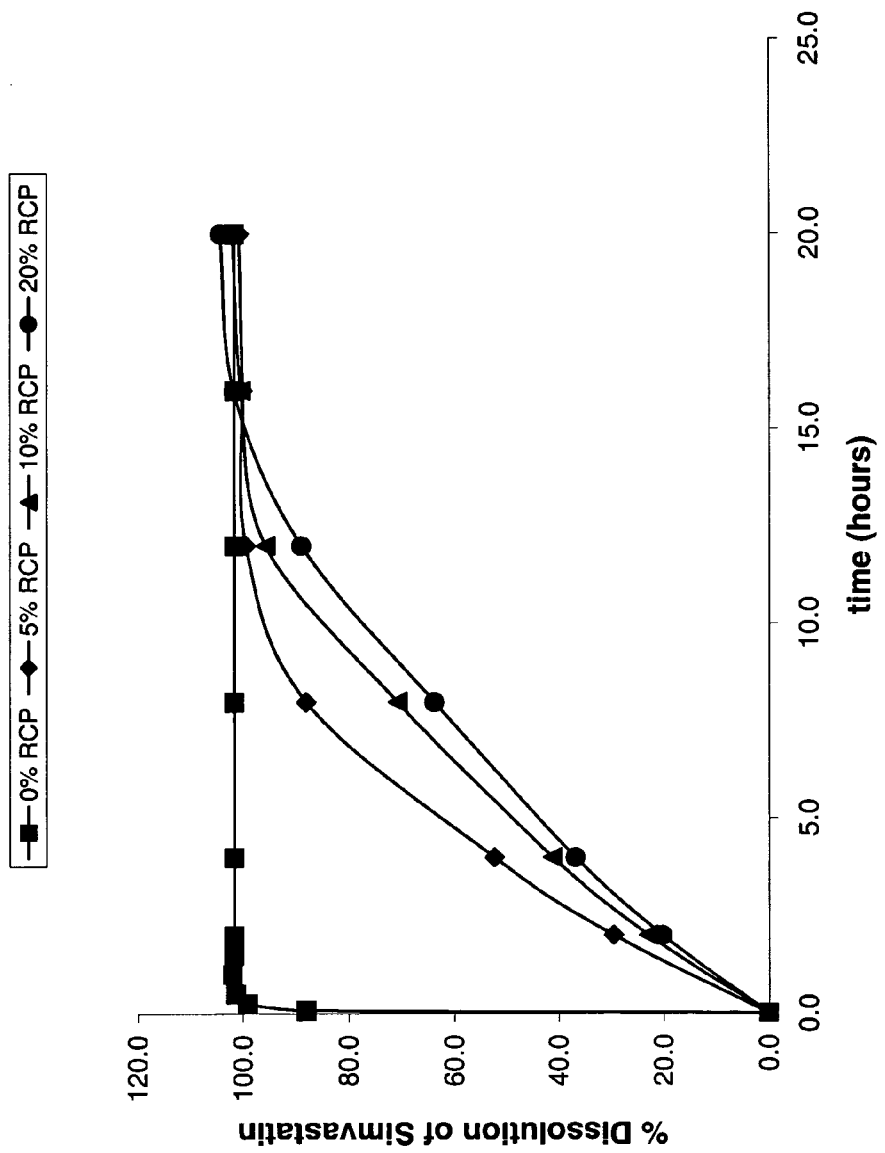
Figure 1. Dissolution of Uncoated Controlled Release Simvastatin

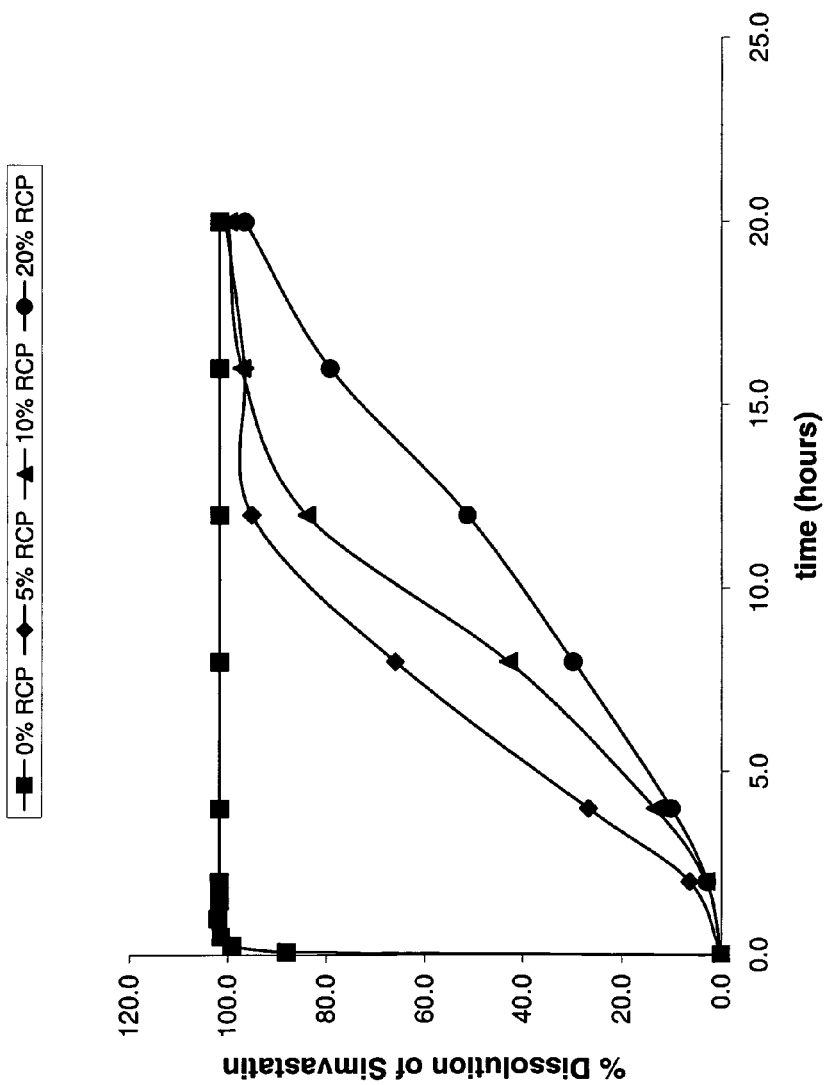
Figure 2. Dissolution of Coated Controlled Release Simvastatin

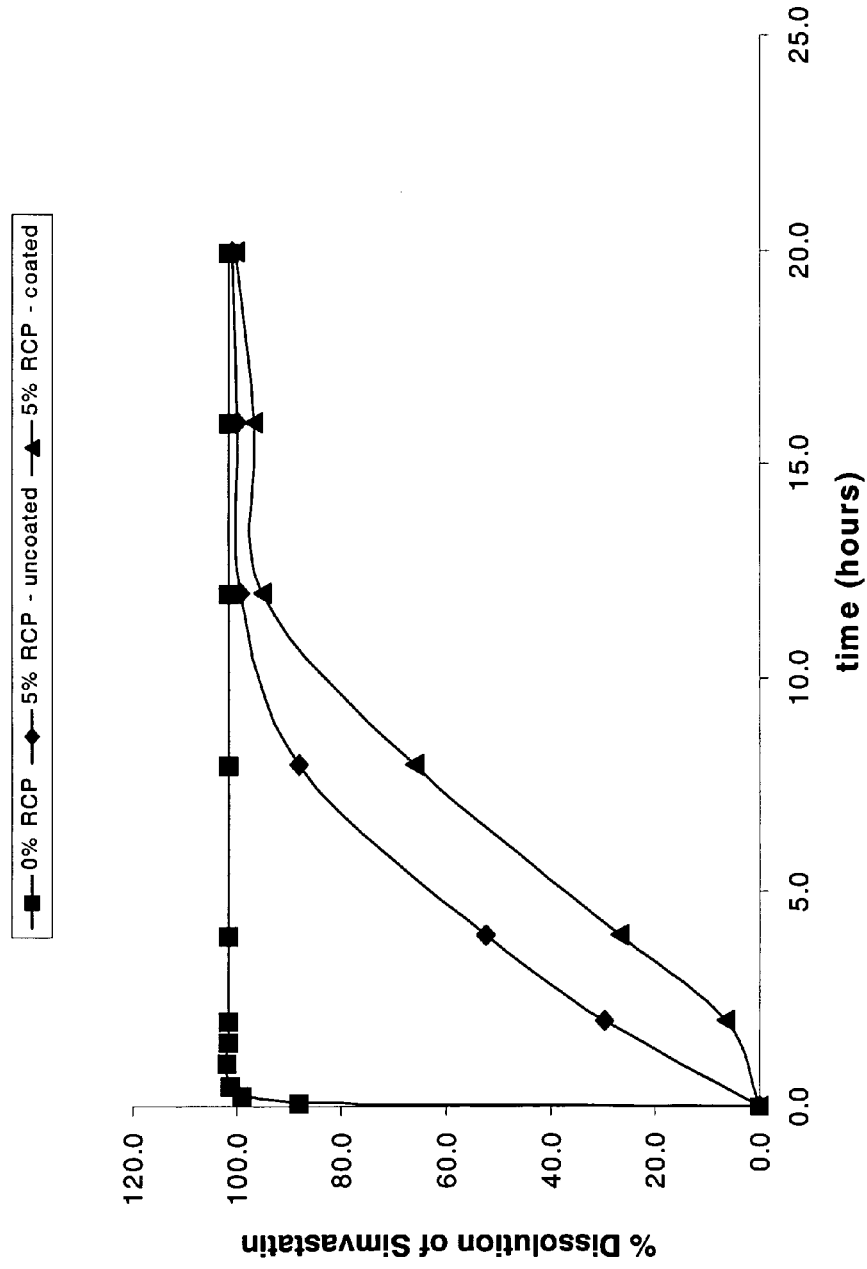
Figure 3. Effect of Coating on Controlled Release of Simvastatin from prototype dosage form containing 5% of the rate controlling polymer (RCP) glyceryl palmitostearate.

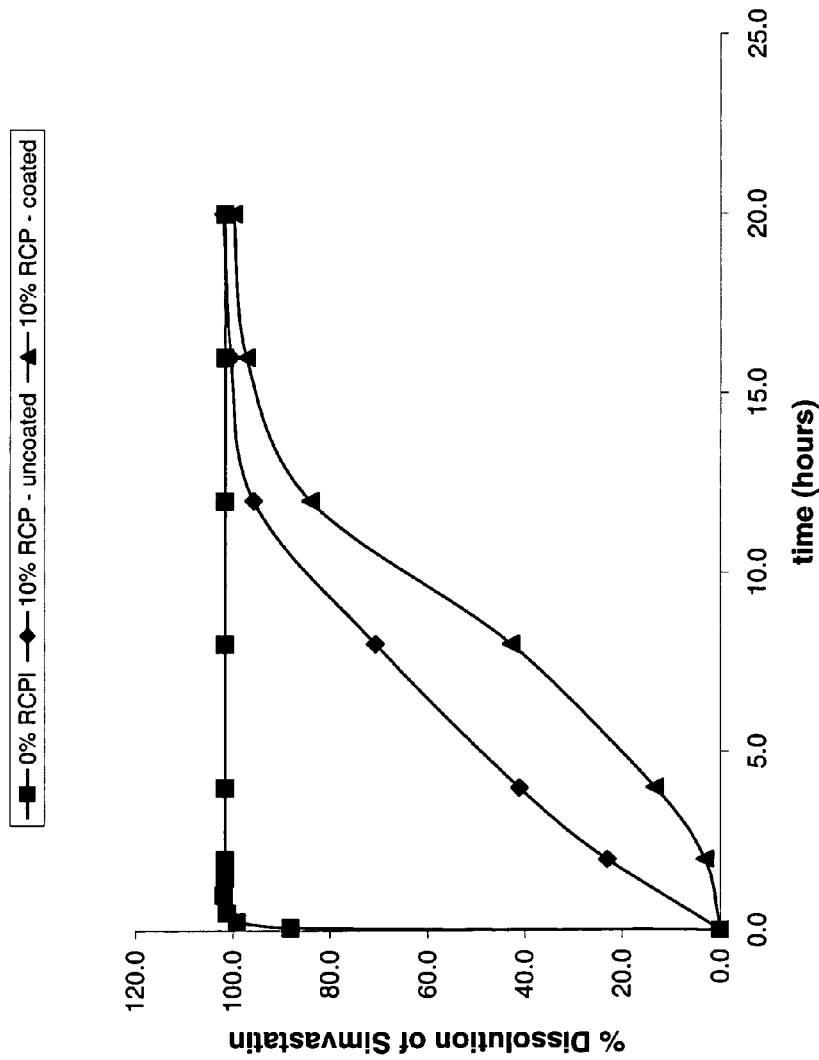
Figure 4. Effect of Coating on Controlled Release of Simvastatin from prototype dosage form containing 10% of the rate controlling polymer (RCP) glyceryl palmitostearate.

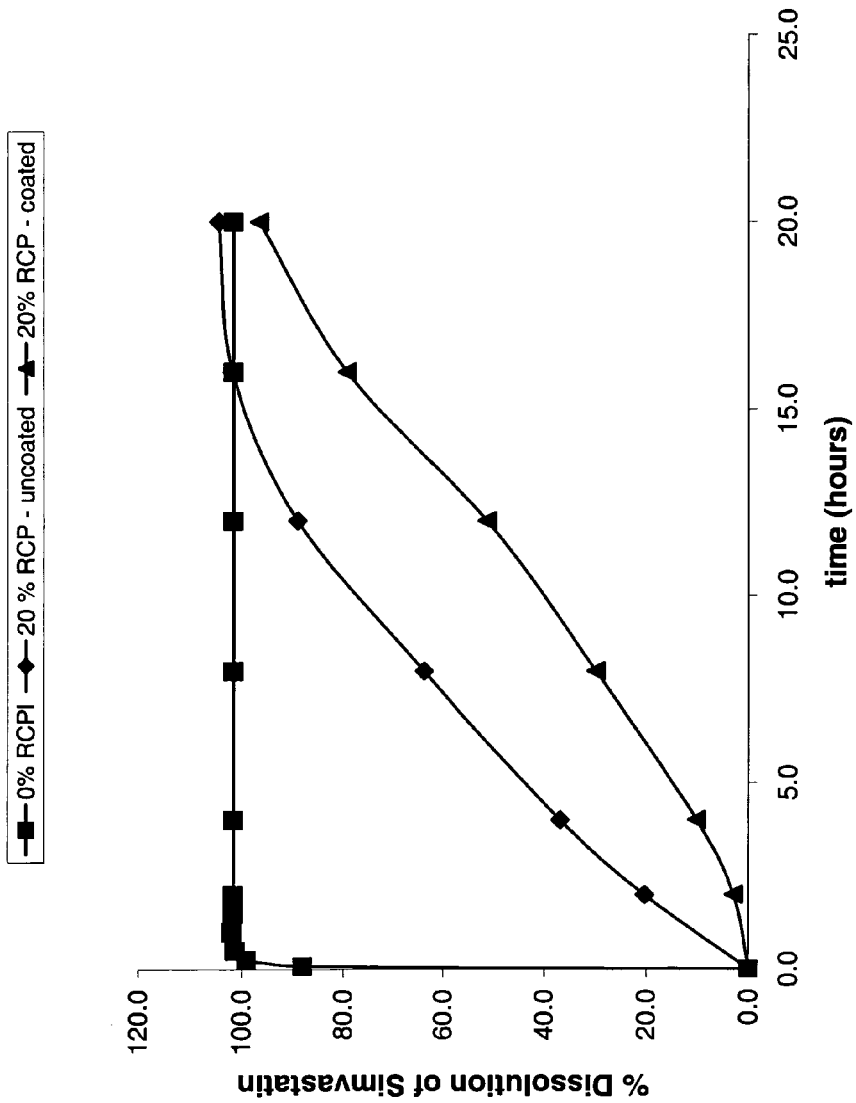
Figure 5. Effect of Coating on Controlled Release of Simvastatin from prototype dosage form containing 20% of the rate controlling polymer (RCP) glyceryl palmitostearate.

METHODS AND COMPOSITION OF EXTENDED DELIVERY OF WATER INSOLUBLE DRUGS

RELATED APPLICATION

This application claims priority of U.S. Provisional Patent Application Ser. No. 60/558,712 filed Apr. 1, 2004, which is incorporated herein by reference.

FIELD OF THE INVENTION

The present invention generally relates to pharmaceutical dosage forms that increase the solubility of water insoluble drugs and also control the release rates of such dosage forms for the extended delivery of pharmaceuticals.

DESCRIPTION OF THE RELATED ART

The advantages of controlled release preparations of therapeutic agents are well established. When a drug release is not controlled, as in an immediate release dosage form, the concentration of drug available in the bloodstream after administration quickly rises and then declines. It is desirable to maintain more constant drug levels over time, allowing administration of fewer doses per day, making patient compliance more likely and reducing the frequency of swings of drug levels in the patient's system. Controlled release preparations are an important means of avoiding an excessively rapid increase in drug concentration with attendant side effects. In addition, such preparations can prevent the drug concentration from falling below therapeutic levels.

Various drug delivery systems commonly referred to as timed-release systems have been developed as controlled release formulations that continuously release amounts of the drug throughout the travel of the drug through the digestive track. For example, U.S. Pat. No. 4,773,907 to Urquhart et al., issued Sep. 27, 1988, discloses a delivery system comprising a capsule containing dosage forms comprising a semi-permeable wall surrounding a compartment containing drug. A passageway through the semi-permeable wall releases drug from the dosage form to the environment. U.S. Pat. No. 4,777,049 to Magruder et al., issued Oct. 11, 1988, discloses an osmotic delivery system. The system provides a device including a wall which can be a laminate comprising a semi-permeable lamina and lamina arrangement with a microporous lamina. The lamina provides micropaths for emitting external fluid into the osmotic device.

U.S. Pat. No. 4,783,337 to Wong et al., issued Nov. 8, 1988, discloses an osmotic system comprising a wall which is at least in part a semi-permeable material that surrounds a compartment. An osmotic composition, or several osmotic compositions, is contained within the compartment defined by the wall and a passageway in the wall connects the first composition with the exterior of the system.

With regard to water insoluble drugs, it is well known in the art that there are solid drugs, which due to their low solubilities have a correspondingly low degree of bioavailability. Several prior art processes have been developed in efforts to increase the solubility and, hence, the bioavailability of poorly soluble pharmaceuticals or drugs. U.S. Pat. Nos. 5,686,133; 5,834,022 and 5,851,275 disclose methods of making a pharmaceutical composition, which include the steps of contacting at least one pharmaceutical ingredient with a mixture of gelatin and lecithin to increase the dissolution rate of water insoluble pharmaceutical ingredients. These patents do not account for controlled release of water insoluble drug product.

There have been several prior art attempts to utilize controlled release technology to deliver water insoluble drugs. U.S. Pat. No. 4,867,985 to Heafield et al. discloses a controlled release pharmaceutical composition for poorly soluble drugs with spheroids, the spheroids containing a water insoluble drug dispersed in a controlled release matrix of microcrystalline cellulose and a cellulose derivative. The water insoluble drug must dissolve in water (pH 5) at 20° C. to a concentration of less than 1.0 mg per ml.

U.S. Pat. No. 5,455,046 to Baichwal et al. discloses a sustained release pharmaceutical formulation that contains a sustained release excipient including a gelling agent, an inert pharmaceutical diluent, and a medicament having moderate to poor solubility. This approach has met with limited acceptance owing to the complexity of the manufacturing processes, which includes mixing of the gelling agent, crosslinking agent and the inert diluent, granulation of the mixture, and coating with a hydrophobic polymer.

U.S. Pat. No. 5,837,379 to Chen et al. discloses a controlled release nifedipine tablet including: (a) a homogeneous compressed core tablet made up of a medicament, a water soluble osmotic compound, one or more osmotic polymers; and (b) a membrane coating which completely covers said core tablet composed of a water insoluble pharmaceutically acceptable polymer and an enteric polymer. A drawback of this formulation with regard to other water insoluble drugs is poor dissolution of the medicament from the dosage form, resulting in poorly controlled release rates. Further, there is a need for harmful organic solvents such as acetone to be used in the coating process during manufacture of the dosage form.

U.S. Pat. No. 6,245,346 to Rothen-Weinhold et al. discloses a pharmaceutical composition for the controlled release of at least one water insoluble active principle combined with a homopolymer of D,L-lactic acid or of L-lactic acid. These formulations are intended primarily for parenteral administration, with release of drug from the polymer matrix over a period of months, which is not amenable to oral delivery of a drug.

In spite of the past efforts to control water insoluble drug release, there exists a need for a methodology to extend the release of broad classes of water insoluble drugs with greater degree of control specificity.

SUMMARY OF THE INVENTION

A pharmaceutical composition is provided that includes an active ingredient in the form of a powder or granule, a water soluble high molecular weight excipient and a water insoluble hydrophilic amphiphilic excipient. These ingredients are solution mixed and dried to form a modified pharmaceutical ingredient in simultaneous contact with both the water soluble high molecular weight excipient and the water insoluble hydrophilic amphiphilic excipient. Adjuvants are compacted about the modified pharmaceutical ingredient as well as a release control agent. The release control agent being present at levels from 1 to 40 total weight percent of the pharmaceutical composition.

A method of making a pharmaceutical composition includes coating at least one pharmaceutical ingredient in the form of a powder or granule with a mixture of water soluble high molecular weight polymer and water insoluble amphiphilic material in solution to form a modified pharmaceutical ingredient. The modified pharmaceutical ingredient is dried and contacted with a release control component present from 1 to 40 total weight percent.

BRIEF DESCRIPTION OF THE DRAWINGS

FIG. 1 is a plot of the dissolution profile of prototype simvastatin_XL dosage forms containing the dissolution enhancing agents gelatin and lecithin alone; with the rate controlling polymer (RCP) glyceryl palmitostearate; and without a neutral methacrylic acid ester coating in a dissolution media of 0.05 M Phosphate Buffer Solution at pH 7.0 with 0.5% sodium lauryl sulfate (SLS).

FIG. 2 is a plot of the dissolution profile of prototype simvastatin_XL dosage forms containing the dissolution enhancing agents gelatin and lecithin alone; with the rate controlling polymer (RCP) glyceryl palmitostearate; and with a neutral methacrylic acid ester coating at a coating level of approximately 1% total dosage form weight in a dissolution media of 0.05 M Phosphate Buffer Solution at pH 7.0 with 0.5% SLS.

FIG. 3 is a plot of the dissolution profile of prototype simvastatin_XL dosage forms containing the dissolution enhancing agents gelatin and lecithin with the rate controlling polymer (RCP) glyceryl palmitostearate, at a level of 5% alone; and with a neutral methacrylic acid ester coating at a coating level of approximately 1% total dosage form weight in a dissolution media of 0.05 M Phosphate Buffer Solution at pH 7.0 with 0.5% SLS.

FIG. 4 is a plot of the dissolution profile of prototype simvastatin_XL dosage forms containing the dissolution enhancing agents gelatin and lecithin with the rate controlling polymer (RCP) glyceryl palmitostearate at a level of 10% alone; and with a neutral methacrylic acid ester coating at a coating level of approximately 1% total dosage form weight in a dissolution media of 0.05 M Phosphate Buffer Solution at pH 7.0 with 0.5% SLS.

FIG. 5 is a plot of the dissolution profile of prototype simvastatin_XL dosage forms containing the dissolution enhancing agents gelatin and lecithin with the rate controlling polymer (RCP) glyceryl palmitostearate at a level of 20% alone; and with a neutral methacrylic acid ester coating at a coating level of approximately 1% total dosage form weight in a dissolution media of 0.05 M Phosphate Buffer Solution at pH 7.0 with 0.5% SLS.

DETAILED DESCRIPTION OF THE PREFERRED EMBODIMENTS

The present invention has utility to modify the time delivery profile of a water insoluble pharmaceutical. The present invention includes a dissolution rate enhancer combined with a suitable hydrophilic or hydrophobic polymer that controls the release of solubilized drug from the polymer matrix. In certain embodiments, the dosage form is coated with a water insoluble permeability controlling membrane. In other embodiments, the dosage form is coated with a pH-dependent polymer.

A method of making a pharmaceutical composition having increased dissolution rate of water insoluble pharmaceutical ingredients and controlled release of the water insoluble pharmaceutical ingredients is disclosed. The method generally includes the steps of first contacting at least one pharmaceutical ingredient with a mixture including a water soluble high molecular weight excipient with a water insoluble hydrophobic amphiphilic excipient in a suitable solvent then combining the mixture with a rate controlling polymer matrix. More than one pharmaceutical ingredient at a time can be treated according to the present invention to yield a desired pharmaceutical composition. Additionally, poorly water soluble pharmaceutical ingredients can be treated according to the present invention and can then be used in combination with other pharmaceutical ingredients, which therefore may or may not be poorly water soluble.

As used herein "poorly water soluble" is used synonymously with "water insoluble" which is defined herein to include compounds having a water solubility at 20° C. of less than 10 mg/ml.

A water soluble high molecular weight excipient according to the present invention includes a variety of high molecular weight polymers that have a molecular weight of between 1,000 and 1,000,000, and a solubility greater than 1 mg/ml. These illustratively include proteins, proteoglycans, dextrin, and glycans. In a preferred embodiment, the water soluble high molecular weight excipient is gelatin.

A water insoluble hydrophobic amphiphilic excipient according to the present invention includes phospholipids, phosphatidylethanolamine, phosphatidylserine phosphatidylinositol, fatty acids triglycerides, bile acids, cholesterol, polyethylene alkyl ethers, and glycerol monostearate and mixtures thereof. In a preferred embodiment, the water insoluble hydrophobic amphiphilic excipient is lecithin.

The term "pharmaceutical ingredient" includes any pharmaceutical compound in solid form such as powder or granules that is poorly water soluble of less than 10 mg/ml; and is used synonymously herein with "drug". The method includes the steps of dissolving a water soluble high molecular weight excipient in a suitable solvent that is heated to between 35°-50° C. The water insoluble amphiphilic material is added to the mixture and is thoroughly mixed therein. At least one pharmaceutical ingredient in solid particulate form is then added slowly and mixed so as to cause thorough and uniform coating of the particles of the pharmaceutical ingredient. Following coating with the mixture, the coated pharmaceutical ingredient is then dried.

The concentration in the coating solution of the soluble high molecular weight material excipient and the insoluble amphiphilic material broadly ranges from approximately 0.001-99.9% (w/v) each and more preferably 0.01% to 2.0% each. The concentration in the coating solution of the pharmaceutical ingredient ranges from approximately 0.1-15.0% (w/v). It is preferable that the soluble high molecular weight material and the insoluble amphiphilic material be present in a 1:1 ratio. The solvent can be any pharmaceutically acceptable solvent. In a preferred embodiment, the solvent is water.

The contacting step includes coating the pharmaceutical ingredient with the mixture including water soluble high molecular weight material, the water insoluble amphiphilic material, and a suitable solvent. The coating step can be accomplished by simple immersion of the particles of the pharmaceutical ingredient. It is believed that the water soluble high molecular weight material coats the particles of the pharmaceutical ingredient and prevents aggregation or clumping of the particles. The water insoluble amphiphilic element is thought to reduce surface tension thereby preventing aggregation or form a microemulsion or to form micelles which facilitate dissolution of the pharmaceutical ingredient. In acting in this complementary fashion, the coating including these agents serves as a dissolution enhancing agent for water insoluble pharmaceutical ingredients. The above-described theory is provided merely for descriptive purposes and is no way intended to limit the scope of the present invention.

After the pharmaceutical ingredient(s) is coated with the dissolution enhancing excipients, the solvent can be removed by various techniques. The solvent removal or drying of the coated pharmaceutical ingredient can be accomplished by lyophilization, or freeze drying, of the coated particles by techniques known to those skilled in the art. Lyophilization, or freeze drying, is a process by which a solid is dissolved or suspended in a liquid, frozen and the water is sublimed from the product after it is frozen. The advantage of this process is that the stability of biologicals and pharmaceuticals that are unstable in the presence of water can be increased without elevated temperatures that often occur during processing (Avis, 1975).

The coated pharmaceutical ingredient can also be dried by the method known in the art as spray drying. Spray drying and fluidized bed processing are widely used in the industry for drying, granulating and coating active ingredients (drugs). These methods enable the pharmaceutical formulator to convert solid drug particles into powders and granulations with excellent flow and compression properties for high speed manufacturing of tablets and capsules. The basic design consists of a spray nozzle, a drying chamber, and an air source. The drug, along with other solubilized or suspended materials, is pumped through a spray nozzle, atomized and dried into a fine, amorphous powder. Alternatively, it is coated onto sugar seeds (nonpareils) or dried into aggregates. The spraying rate, air flow and temperature of the drying chamber all can be varied to produce the desired end product. This process is widely used in the pharmaceutical industry and the invention described in this patent has been shown to be manufacturable by this method.

The coated pharmaceutical ingredient can also be granulated to obtain granules having good redispersability in water with granule diameters in the range of 4-1000 microns. The granulation can be accomplished using a fluid bed granulator (Glatt, Ramsey, N.J.) using means well known to those skilled in the art.

Additionally, the method of the present invention can include the step of spray coating the dissolution enhanced coated pharmaceutical ingredient onto micronized particles. Micronization is the process by which solid drug particles are reduced in size. Since the dissolution rate is directly proportional to the surface area of the solid, and reducing the particle size increases the surface area, reducing the particle size increases the dissolution rate.

It is an aspect of the present invention that release of water insoluble drug is controlled by the addition of release control components in addition to other pharmaceutically acceptable fillers, binders, and lubricants. The release control component being present from 1-40 total weight percent, preferably from 5-20 total weight percent with the appreciation that the release rate decrease with increasing amount of release control component present. In a preferred embodiment, atomized glyceryl palmitostearate is the release control components in the drug delivery system of the present invention. Additional operative release control components according to the present invention include: alpha-starch, gum arabic, hydroxypropylcellulose, carboxymethylcellulose, polyvinylpyrrolidone, acrylic copolymers such as acrylate/alkylacrylate copolymers, polyacrylamides, polysaccharides, hydroxypropylmethylcellulose, natural gums and clays, and, as lipophilic gelling agents, representative thereof are the modified clays such as bentones, fatty acid metal salts such as aluminum stearates, hydrophobic silica, hydroxypropylmethyl cellulose, sodium carboxymethyl cellulose, hydroxyethyl cellulose, polyethylenes and ethylcellulose and a PEG of appropriate molecular weight.

In a preferred embodiment, a filler in the excipient formulation of the present invention is lactose. Further examples of fillers which may be used in the present invention illustratively include starches, saccharides, sucrose, glucose, mannitol, and silicic acid.

In a preferred embodiment, magnesium stearate is a lubricant in the present invention. Further examples of lubricants which may be used in the present invention illustratively include talc, calcium stearate, solid polyethylene glycols, sodium lauryl sulfate, or mixtures thereof. The excipient formulation may further contain inert customary ingredients or carriers such as sodium citrate or dicalcium phosphate and (a) binders, as for example, carboxymethylcellulose, alginates, gelatin, polyvinylpyrrolidone, sucrose, and acacia; (b) humectants, as for example, glycerol; (c) disintegrating agents, as for example, agar-agar, calcium carbonate, potato or tapioca starch, alginic acid, certain complex silicates, and sodium carbonate; (d) solution retarders, as for example paraffin; (e) absorption accelerators, as for example, quaternary ammonium compounds; (f) wetting agents, as for example, cetyl alcohol, and glycerol monostearate; and (g) adsorbents, as for example, kaolin and bentonite.

Besides such inert diluents, the excipient formulation can also include adjuvants, such as emulsifying and suspending agents, sweetening, flavoring, and perfuming agents.

In a preferred embodiment, the water insoluble drug is the cholesterol lowering agent, simvastatin. Examples of other drugs currently on the market that fall into the category of water insoluble drugs are listed in Table 1.

TABLE 1

| Examples of Water Insoluble Drugs |
| Drug |
| --- |
| Cyclosporin |
| Griseofulvin |
| Digoxin |
| Nifedipine |
| Itraconazole |
| Carbamazepine |
| Piroxicam |
| Fluconazole |
| Finasteride |
| Diflunisal |
| Lovastatin |
| Simvastatin |
| Glipizide |

In a further aspect of the present invention, the resultant dosage form can be coated with a variety of water permeability controlling agents. In a preferred embodiment, the film coating is a neutral methacrylic acid ester. Other examples of composition for the water permeability controlling agents are cellulose acetate, cellulose acetate butyrate, ethylcellulose and combinations of the above.

In a further embodiment, the water permeability controlling agent is a pH responsive material such as cellulose acetate phthalate, methylcellulose phthalate, hydroxyethylcellulose, cellulose acetate tetrahydrophthalate, cellulose acetate hexahydrophthalate, methyl-methacrylate, methacrylic acid, and combinations thereof.

EXAMPLE

A prototype dosage form containing the cholesterol lowering drug simvastatin is presented to illustrate the methodology for controlled release of a water insoluble drug. This example is intended to illustrate a particular embodiment of the invention and is not intended to limit the scope of the specification, including the claims, in any way. Simvastatin, a lipid lowering agent with an aqueous solubility of 0.005 mg/ml at 37° C., is coated with gelatin, a water soluble, high molecular weight material and lecithin, a water insoluble amphiphilic material as described above. The final % concentrations for the simvastatin, gelatin and lecithin (referred to as SGL) used for this example are presented in Table 2. The suspension is then placed on a freeze drier and the moisture is removed by lyophilization.

TABLE 2

Simvastatin, Gelatin, and Lecithin Composition

| Ingredients | % |
|---|---|
| Simvastatin | 50.0 |
| Gelatin | 25.0 |
| Lecithin | 25.0 |

Lyophilization is continued for 24-36 hours at a shelf temperature of −40° Centigrade. After that time, the shelf temperature is gradually raised to 0° C. with continued applied vacuum. The dried material is sequentially sieved through #4, 10, 20, 25, and 30 sieves and stored over desiccant at room temperature until compounded. As illustrated in Table 3, the lecithin and gelatin coated simvastatin showed a >5000-fold increase in solubility in water at 37° C.

TABLE 3

Simvastatin Solubility in Water at 37° C.

| Formulation | Solubility (µg/mL) |
|---|---|
| Bulk Drug | <0.01 |
| SGL (1:1:2) | 67.50 |

The remaining excipients listed in Table 4 are added by geometric mixing of material. The final formulation is a mixture of the SGL powder (Table 2) and other excipients which include glyceryl palmitostearate, lactose, magnesium stearate, and a dissolution enhancer. The dissolution enhancer being conventional to the art and illustratively including a cross-linked carboxymethyl ether of a polysaccharide. A 2.5% carboxymethylated potato starch is a specific example of a dissolution enhancer. For the purpose of this example, the levels of active component, a dissolution enhancer, and magnesium stearate are fixed. The glyceryl palmitostearate levels are adjusted for release control and the lactose was adjusted accordingly to maintain the weight and size of the compact. The tableted compacts are formed by compressing the mixture in size 2 punch and die set. The target compact weight is 213 mg.

TABLE 4

Simvastatin - XL Tablet Composition

| Ingredients | % |
|---|---|
| SGL formulation | 44.2 |
| Glyceryl palmitostearate | 5.0-20.0 |
| Lactose | 34.3-49.3 |
| Magnesium stearate | 1.0 |
| Dissolution enhancer | 0.5 |

The prototype dosage form is coated with a water insoluble but water permeable polymer of a neutral methacrylic acid ester. A solution containing a 4:2:1 weight ratio of a neutral methacrylic acid ester, glyceryl triacetate, and a homopolymer consisting of N-vinyl pyrrolidone in ethanol is used. The solution is heated to approximately 45-50°, and the tableted dosage forms are dipped into the solution, then removed and dried. The process is repeated until the desired coating level of typically between 0.5-3 total weight percent is reached. Preferably, the coating level is approximately 1 total weight percent.

In vitro dissolution experiments are performed using a Vankel USP dissolution apparatus maintained at 37° C. with a paddle speed of 50 rpm. The dissolution medium used is 0.05 M Phosphate Buffer Solution at pH 7.0 with 0.5% sodium lauryl sulfate. The drug concentrations are determined using HPLC analysis. The dissolution profiles are presented in FIGS. 1-5 and the calculated dissolution rates are given in Table 5.

TABLE 5

Dissolution Rates of Simvastatin from Prototype Dosage Forms.

| Dosage form | Dissolution rate % drug released/hour |
|---|---|
| SGL formulation Uncoated | 1057.0 |
| SGL with 5% glyceryl palmitostearate Uncoated | 10.8 |
| SGL with 10% glyceryl palmitostearate Uncoated | 8.7 |
| SGL with 20% glyceryl palmitostearate Uncoated | 7.9 |
| SGL with 5% glyceryl palmitostearate - 1% permeable film coating | 8.6 |
| SGL with 10% glyceryl palmitostearate - 1% permeable film coating | 5.6 |
| SGL with 20% glyceryl palmitostearate - 1% permeable film coating | 3.9 |

As can be seen in FIG. 1, addition of glyceryl palmitostearate to the dosage forms at levels of 5-20 weight percent of the total tablet yields linear release of drug from the dosage form (zero order control) over at least a 12 hour period in contrast to prototype dosage form without glyceryl palmitostearate which shows immediate release of the drug. Coating of the dosage form with the water permeability-controlling polymer yields additional control of the drug release rate (FIG. 2). As shown in FIGS. 3-5 and as seen in Table 5, at any given level of the rate controlling polymer, coating with a permeability controlling polymer reduces the dissolution rate. While this example shows control of the drug dissolution rate between 3.9-10.8% per hour, it is recognized that dissolution release rates between 2% per hour up to 25% per hour can be achieved through use of the release control components and permeability control polymers by those skilled in the art.

CITED LITERATURE

Avis, "Remington's Pharmaceutical Sciences", Parenteral Preparations, Mack Publishing Company 15th edition, pp. 1483-1485 (1975).
Jones, "Fluidized Bed Processing and Drying" *Int. Soc. of Pharm. Eng.* pp. 1-7 (1991).

The invention claimed is:
1. A pharmaceutical composition comprising:
a pharmaceutical ingredient in the form of a powder or granule;
a water soluble high molecular weight excipient of molecular weight between 1,000 and 1,000,000 Daltons;
a water insoluble hydrophilic amphiphilic excipient, wherein said pharmaceutical ingredient, said water soluble high molecular weight excipient, and said water insoluble hydrophilic amphiphilic excipient are solution mixed and dried to form a modified pharmaceutical ingredient in simultaneous contact with both said water soluble high molecular weight excipient and said water insoluble hydrophilic amphiphilic excipient; and a release control agent compacted about said modified pharmaceutical ingredient and present at levels from 1 to 40 total weight percent.

2. The composition of claim 1 further comprising adjuvants compacted about said modified pharmaceutical ingredient.

3. The composition of claim 1 wherein said pharmaceutical ingredient is selected from the group consisting of: cyclosporin, griseofulvin, digoxin, nifedipine, itraconazole, carbamazepine, piroxicam, fluconazole, finasteride, diflunisal, lovastatin, simvastatin and glipizide.

4. The composition of claim 1 wherein said pharmaceutical ingredient is simvastatin.

5. The composition of claim 1 wherein .said water soluble high molecular weight excipient is selected from the group consisting of: proteins, proteoglycans, dextrin and glycans.

6. The pharmaceutical composition of claim 1 wherein said water soluble high molecular weight excipient is gelatin.

7. The composition of claim 1 wherein said water insoluble hydrophobic amphiphilic excipient is selected from the group consisting of: phospholipids, phosphatidylethanolamine, phosphatidylserine phosphatidylinositol and fatty acid triglycerides.

8. The pharmaceutical composition of claim 1 wherein said water insoluble hydrophobic amphiphilic excipient is lecithin.

9. The composition of claim 1 wherein said release control agent is glyceryl palmitostearate present from 5 to 40 total weight percent.

10. The composition of claim 1 wherein said release control agent is selected from the group consisting of: alpha-starch, gum arabic, hydroxypropylcellulose, carboxymethylcellulose, polyvinylpyrrolidone, acrylic copolymers, acrylate/alkylacrylate copolymers, polyacrylamides, polysaccharides, hydroxypropylmethylcellulose, natural gums and clays, lipophilic gelling agents, modified clays, bentones, fatty acid metal salts, aluminum stearates, hydrophobic silica, hydroxypropylmethyl cellulose, sodium carboxymethyl cellulose, hydroxyethyl cellulose, polyethylenes, ethylcellulose, and a PEG of appropriate molecular weight.

11. The pharmaceutical composition of claim 1 whereby said composition is coated with a water permeability controlling agent selected from the group consisting of: neutral methacrylic acid ester, cellulose acetate, cellulose acetate butyrate, ethyl cellulose and combinations thereof.

12. The composition of claim 1 wherein said release control agent is present in an amount such that said pharmaceutical ingredient has a dissolution rate proportional to the amount of said release control agent present.

13. The composition of claim 11 wherein said water permeability controlling agent is present to between 0.5 to 3 total weight percent.

14. A method of making a pharmaceutical composition comprising:
coating at least one pharmaceutical ingredient with a mixture consisting essentially of a water soluble high molecular weight polymer of molecular weight between 1,000 and 1,000,000 Daltons and a water insoluble amphiphilic component in solution to form a modified pharmaceutical ingredient;

drying said modified pharmaceutical ingredient; and contacting the dry modified pharmaceutical ingredient with a release control component present from 1 to 40 total weight percent where said release control agent is selected from the group consisting of: glycervl palmitosterate, alpha-starch, gum arabic, hydroxypropylcellulose, carboxymethylcellulose , polyvinylpyrrolidone, acrylic copolymers, acrylate/alkylacrylate copolymers, polyacrylamides, polysaccharides, hydroxypropylmethylcellulose, natural gums and clays, lipophilic gelling agents, modified clays, bentones, fatty acid metal salts, aluminum stearates, hydrophobic silica, hydroxypropylmethyl cellulose, sodium carboxymethyl cellulose, hydroxyethyl cellulose, polyethylenes, ethylcellulose, and a PEG of appropriate molecular weight.

15. The method of claim 14 wherein said release control agent is glyceryl palmitostearate.

16. The method of claim 14 further comprising over layering said release control agent with a water permeability control agent.

17. The method of claim 14 wherein contacting the dry modified pharmaceutical ingredient with the release control agent comprises the step of compacting the release control agent and the dry modified pharmaceutical ingredient.

18. The method of claim 14 wherein said pharmaceutical ingredient is selected from the group consisting of cyclosporin, griseofulvin, digoxin, nifedipine, itraconazole, carbamazepine, piroxicam, fluconazole, finasteride, diflunisal, lovastatin, simvastatin and glipizide.

19. The method of claim 14 wherein said pharmaceutical ingredient is simvastatin.

20. The method of claim 14 wherein said water soluble high molecular weight excipient is selected from the group consisting of: proteins, proteoglycans, dextrin and glycans.

21. The method of claim 14 wherein said water soluble high molecular weight excipient is gelatin.

22. The method of claim 14 wherein said water insoluble hydrophobic amphiphilic excipient is selected from the group consisting of: phospholipids, phosphatidylethanolamine, phosphatidylserine phosphatidylinositol and fatty acid triglycerides.

23. The method of claim 14 wherein said water insoluble hydrophobic amphiphilic excipient is lecithin.

24. A pharmaceutical composition comprising:
a pharmaceutical ingredient in the form of a powder or granule;
a water soluble high molecular weight excipient of molecular weight between 1,000 and 1,000,000 Daltons;
a water insoluble hydrophilic amphiphilic excipient, wherein said pharmaceutical ingredient, said water soluble high molecular weight excipient, and said water insoluble hydrophilic amphiphilic excipient are solution mixed and dried to form a modified pharmaceutical ingredient in simultaneous contact with both said water soluble high molecular weight excipient and said water insoluble hydrophilic amphiphilic excipient; and a release control agent compacted about said modified pharmaceutical ingredient, said release control agent selected from the group consisting of: glyceryl palmitostearate, alpha-starch, gum arabic, hydroxypropylcellulose, carboxymethylcellulose, polyvinylpyrrolidone, acrylic copolymers, acrylate/alkylacrylate copolymers, polyacrylamides, polysaccharides, hydroxypropylmethylcellulose, natural gums and clays, lipophilic gelling agents, modified clays, bentones, fatty acid metal salts, aluminum stearates, hydrophobic silica, hydroxypropylmethyl cellulose, sodium carboxymethyl cellulose, hydroxyethyl cellulose, polyethylenes, ethylcellulose, and a PEG of appropriate molecular weight.

25. The composition of claim 24 wherein said release control agent is present from 5 to 40 total weight percent.

26. A pharmaceutical composition comprising:
a pharmaceutical ingredient in the form of a powder or granule;
a water soluble high molecular weight excipient of molecular weight between 1,000 and 1,000,000 Daltons;
a water insoluble hydrophilic amphiphilic excipient, wherein said pharmaceutical ingredient, said water soluble high molecular weight excipient, and said water insoluble hydrophilic amphiphilic excipient are solution mixed and dried to form a modified pharmaceutical ingredient in simultaneous contact with both said water soluble high molecular weight excipient and said water insoluble hydrophilic amphiphilic excipient; and glyceryl palmitostearate compacted about said modified pharmaceutical ingredient.

27. The composition of claim 25 wherein said glyceryl palmitosterate is present from 5 to 40 total weight percent.

* * * * *

UNITED STATES PATENT AND TRADEMARK OFFICE
CERTIFICATE OF CORRECTION

PATENT NO. : 8,535,716 B2
APPLICATION NO. : 11/097487
DATED : September 17, 2013
INVENTOR(S) : Hilfinger et al.

Page 1 of 1

It is certified that error appears in the above-identified patent and that said Letters Patent is hereby corrected as shown below:

In the Claims

Column 9, claim 5, line 20, Delete ".said", Insert --said--.

Column 10, claim 14, line 5, Delete "glycervl", Insert --glyceryl--.

Signed and Sealed this
Ninth Day of September, 2014

Michelle K. Lee
*Deputy Director of the United States Patent and Trademark Office*